US008388992B2

(12) United States Patent
Luu et al.

(10) Patent No.: US 8,388,992 B2
(45) Date of Patent: Mar. 5, 2013

(54) ANTI-MICROBIAL HAND TOWEL WITH TIME-DELAY CHROMATIC TRANSFER INDICATOR AND ABSORBENCY RATE DELAY

(75) Inventors: Phuong Van Luu, Appleton, WI (US); Anthony O. Awofeso, Appleton, WI (US); Craig D. Yardley, Roswell, GA (US); Kang Chang Yeh, Neenah, WI (US); Bruce W. Janda, Hortonville, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 695 days.

(21) Appl. No.: 11/728,407

(22) Filed: Mar. 26, 2007

(65) Prior Publication Data

US 2007/0237807 A1    Oct. 11, 2007

Related U.S. Application Data

(60) Provisional application No. 60/786,819, filed on Mar. 28, 2006.

(51) Int. Cl.
*A01N 25/34* (2006.01)
(52) U.S. Cl. ........ 424/414; 424/400; 424/402; 424/404; 424/443
(58) Field of Classification Search ................... 424/414
See application file for complete search history.

(56) References Cited

U.S. PATENT DOCUMENTS

| | | | |
|---|---|---|---|
| 3,946,611 A | 3/1976 | Larsson et al. | 73/356 |
| 4,029,598 A | 6/1977 | Neisius et al. | 436/163 |
| 4,078,071 A | 3/1978 | Walker | 514/399 |
| 4,231,370 A | 11/1980 | Mroz et al. | 604/361 |
| 4,248,597 A * | 2/1981 | McNeely | 116/206 |
| 4,705,513 A | 11/1987 | Sheldon et al. | 604/361 |
| 4,767,625 A | 8/1988 | Mitsuno et al. | 424/401 |
| 4,987,632 A | 1/1991 | Rowe et al. | 15/104.93 |
| 5,197,958 A | 3/1993 | Howell | 604/361 |
| 5,240,562 A | 8/1993 | Phan et al. | 162/158 |
| 5,354,289 A | 10/1994 | Mitchell et al. | 604/361 |
| 5,389,093 A | 2/1995 | Howell | 604/361 |
| 5,427,696 A | 6/1995 | Phan et al. | 162/158 |
| 5,468,236 A | 11/1995 | Everhart et al. | 604/361 |
| 5,525,345 A | 6/1996 | Warner et al. | 424/402 |
| 5,607,760 A | 3/1997 | Roe | 442/375 |
| 5,624,676 A | 4/1997 | Mackey et al. | 424/414 |
| 5,665,426 A | 9/1997 | Krzysik et al. | 427/211 |
| 5,690,624 A | 11/1997 | Sasaki et al. | 604/361 |
| 5,705,164 A | 1/1998 | Mckey et al. | 424/400 |
| 5,716,692 A | 2/1998 | Warner et al. | 424/153 |
| 5,720,966 A | 2/1998 | Ostenforf | 424/402 |
| 5,781,942 A | 7/1998 | Allen et al. | 4/623 |
| 5,830,487 A | 11/1998 | Klofta et al. | 424/402 |
| 5,869,075 A | 2/1999 | Krzysik | 424/41 |
| 5,871,763 A | 2/1999 | Luu et al. | 424/402 |
| 5,882,573 A | 3/1999 | Kwok et al. | 264/510 |
| 5,902,540 A | 5/1999 | Kwok | 264/555 |
| 5,904,298 A | 5/1999 | Kwok et al. | 239/135 |
| 5,945,910 A | 8/1999 | Gorra | 340/573.1 |
| 5,980,922 A | 11/1999 | Mackey et al. | 424/402 |
| 5,981,044 A | 11/1999 | Phan et al. | 428/212 |
| 5,994,414 A | 11/1999 | Franco et al. | 516/74 |
| 6,001,381 A | 12/1999 | Gordon et al. | 424/402 |
| 6,007,797 A | 12/1999 | Bell et al. | 424/59 |
| 6,075,178 A | 6/2000 | Wilhelm et al. | 604/361 |
| 6,183,763 B1 | 2/2001 | Beerse et al. | 424/404 |
| 6,207,274 B1 | 3/2001 | Ferenc et al. | 428/364 |
| 6,210,695 B1 | 4/2001 | Beerse et al. | 424/404 |
| 6,238,682 B1 | 5/2001 | Klofta et al. | 424/402 |
| 6,248,593 B1 | 6/2001 | Esswein et al. | 436/77 |
| 6,258,368 B1 | 7/2001 | Beerse et al. | 424/404 |
| 6,270,783 B1 | 8/2001 | Slavtcheff et al. | 424/402 |
| 6,284,259 B1 | 9/2001 | Beerse et al. | 424/404 |
| 6,297,424 B1 | 10/2001 | Olsen et al. | 604/361 |
| 6,307,119 B1 | 10/2001 | Cammarota et al. | 604/361 |
| 6,309,655 B1 | 10/2001 | Minnix | 424/401 |
| 6,322,801 B1 | 11/2001 | Lorenzi et al. | 424/402 |
| 6,352,700 B1 * | 3/2002 | Luu et al. | 424/402 |
| 6,383,505 B1 | 5/2002 | Kaiser et al. | 424/407 |
| 6,391,626 B1 | 5/2002 | Adams et al. | 435/287.9 |
| 6,433,244 B1 | 8/2002 | Roe et al. | 604/361 |
| 6,436,885 B2 | 8/2002 | Biedermann et al. | 510/131 |
| 6,468,392 B2 * | 10/2002 | Oriarian et al. | 162/109 |
| 6,482,423 B1 | 11/2002 | Beerse et al. | 424/404 |
| 6,488,943 B1 | 12/2002 | Beerse et al. | 424/401 |
| 6,501,002 B1 | 12/2002 | Roe et al. | 604/362 |

(Continued)

FOREIGN PATENT DOCUMENTS

| | | |
|---|---|---|
| EP | 0 875 233 A1 | 11/1998 |
| EP | 1 050 297 A1 | 11/2000 |

(Continued)

OTHER PUBLICATIONS

Chemical Activities Teacher Edition, Acids & Bases in the Bathroom and Kitchen, Christi L. Borgford et al., Sec. 47.
Chemical Activities Teacher Edition, Enzymes in Saliva, Christie L. Borgford et al., Sec. 69.
Chemical Activities Teacher Edition, Tests for Protein, Christie L. Borgford et al., Sec. 75, (1988).
Chemical Activities Teacher Edition, Chemistry of Invisible Inks, Christie L. Borgford et al., Sec. 95.
Chemical Activities Teacher Edition, Identifying the Mystery Metal, Christie L. Borgford et al., Sec. 96, (1988).
Chemical Demonstrations, A Sourcebook for Teachers, Precipitate Formation: Blue, Lee R. Summerlin et al., Sec. 14, (1985).
Chemical Demonstrations, A Sourcebook for Teachers, The Effect of Temperature on a Hydrate: Pink to Blue, Lee R. Summerlin et al., Sec. 19.

(Continued)

*Primary Examiner* — Daniel Sullivan
*Assistant Examiner* — Barbara Frazier
(74) *Attorney, Agent, or Firm* — Laura L. Bozek

(57) ABSTRACT

A disposable paper towel with an anti-microbial lotion and is provided with a chromatic transfer indicator which undergoes a delayed, visually perceptible color change at a predetermined time after the towel is wetted. An anti-microbial lotion on the towel increases water absorbency times (WAR) to further promote lotion transfer to the skin and increase lotion transfer effectiveness.

65 Claims, 4 Drawing Sheets
(2 of 4 Drawing Sheet(s) Filed in Color)

U.S. PATENT DOCUMENTS

| | | |
|---|---|---|
| 6,515,194 B2 | 2/2003 | Neading et al. .............. 604/361 |
| 6,576,810 B1 | 6/2003 | Underhill et al. ............ 604/361 |
| 6,596,918 B1 | 7/2003 | Wehrle et al. ................ 604/361 |
| 6,610,312 B2 | 8/2003 | Farrell et al. .................. 424/401 |
| 6,635,797 B2 | 10/2003 | Olson et al. ................... 604/361 |
| 6,641,825 B2 | 11/2003 | Scholz et al. ................. 424/401 |
| 6,645,611 B2 | 11/2003 | Seth ......................... 428/311.11 |
| 6,645,930 B1 | 11/2003 | Wallis et al. .................. 510/438 |
| 6,733,766 B2 | 5/2004 | Gott et al. ..................... 424/401 |
| 6,832,916 B2 | 12/2004 | Collopy ........................ 424/236 |
| 6,904,865 B2 | 6/2005 | Klofta et al. .................. 116/206 |
| 6,949,089 B2 | 9/2005 | Olson et al. ............. 604/385.01 |
| 7,169,400 B2 | 1/2007 | Luu et al. ...................... 424/400 |
| 7,258,764 B2 | 8/2007 | Mauler ......................... 162/158 |
| 2002/0002124 A1 | 1/2002 | Biedermann et al. ......... 510/218 |
| 2002/0031486 A1 | 3/2002 | Lunsmann et al. ........ 424/70.28 |
| 2002/0061500 A1 | 5/2002 | Collopy ........................ 424/238 |
| 2003/0064091 A1 | 4/2003 | Kinderdine et al. ............ 424/443 |
| 2003/0073966 A1 | 4/2003 | Sosalla et al. ................. 604/443 |
| 2003/0086962 A1 | 5/2003 | Westerfield et al. .......... 424/443 |
| 2003/0091618 A1 | 5/2003 | Seth et al. ..................... 424/443 |
| 2003/0113364 A1 | 6/2003 | McAtee et al. ................ 424/443 |
| 2003/0135186 A1 | 7/2003 | Olson et al. ............. 604/385.01 |
| 2003/0143263 A1 | 7/2003 | Durden et al. ................ 424/443 |
| 2003/0154904 A1 | 8/2003 | Klofta et al. .................. 116/206 |
| 2003/0164136 A1 | 9/2003 | Klofta et al. .................. 116/206 |
| 2003/0206878 A1 | 11/2003 | Gott et al. |
| 2003/0206940 A1 | 11/2003 | Gott et al. ..................... 424/443 |
| 2003/0211124 A1* | 11/2003 | Luu et al. ...................... 424/401 |
| 2004/0039353 A1 | 2/2004 | Koenig et al. .................. 604/56 |
| 2004/0144510 A1* | 7/2004 | Mauler .......................... 162/158 |
| 2004/0191118 A1 | 9/2004 | Mody ............................ 422/56 |
| 2004/0238135 A1 | 12/2004 | Edwards et al. .............. 162/111 |
| 2004/0250969 A1* | 12/2004 | Luu et al. ...................... 162/123 |
| 2005/0031847 A1 | 2/2005 | Martens et al. ............. 428/321.5 |
| 2005/0160543 A1 | 7/2005 | Catalfamo et al. ........ 15/104.93 |
| 2005/0217814 A1 | 10/2005 | Super et al. ................... 162/111 |
| 2005/0241786 A1 | 11/2005 | Edwards et al. .............. 162/109 |
| 2005/0241787 A1 | 11/2005 | Murray et al. ................ 162/113 |
| 2005/0279471 A1 | 12/2005 | Murray et al. ................ 162/111 |
| 2006/0110432 A1* | 5/2006 | Luu et al. ...................... 424/443 |
| 2006/0237154 A1 | 10/2006 | Edwards et al. .............. 162/111 |
| 2006/0289133 A1 | 12/2006 | Yeh et al. |
| 2006/0289134 A1 | 12/2006 | Yeh et al. |

FOREIGN PATENT DOCUMENTS

| | | |
|---|---|---|
| WO | WO 95/06102 | 3/1995 |
| WO | WO 97/30216 | 8/1997 |
| WO | 9746205 A2 | 12/1997 |
| WO | 9945771 A1 | 9/1999 |

OTHER PUBLICATIONS

Chemical Demonstrations, A Sourcebook for Teachers, A Traffic Light Reaction, Lee R. Summerlin et al, Sec. 50, (1985).

Chemical Demonstrations, A Sourcebook for Teachers, The Silver Mirror Reaction, Lee R. Summerlin et al., Sec. 58.

Chemical Demonstrations, A Sourcebook for Teachers, Magic Writing Reactions, Lee R. Summerlin et al., Sec. 91, (1985).

Chemical Demonstrations, A Sourcebook for Teachers, Patriotic Colors: Red, White, and Blue, Lee R. Summerlin et al., Sec. 92, (1985).

Chemical Demonstrations, A Handbook for Teachers of Chemistry, Bassam Z. Shakhashiri, vol. 3, p. 56.

Chemical Demonstrations, A Handbook for Teachers of Chemistry, Bassam Z. Shakhashiri, vol. 3, pp. 146-151, (1989).

Fun With Chemistry, A Guidebook of K-12 Activities From the Institute for Chemical Education, vol. 1, pp. 189-194, (1991).

Journal of Chemical Education, Indicators: A Historical Perspective, Ferenc Szabadváry, 1964, vol. 41, No. 5, pp. 285-287, (1964).

Journal of Chemical Education, Plant Pigments as Acid-Base Indicators—An Exercise for the Junior High School, Mary Forster, 1978, vol. 55, No. 2, pp. 107-108.

Journal of Chemical Education, Edible Acid-Base Indicators, Robert C. Mebane et al., 1985, vol. 62, No. 3, pp. 285.

Journal of Chemical Education, Anthocyanins: Model Compounds for Learning About More than pH, Robert Cutright et al., 1996, vol. 73, No. 4, pp. 306-309.

Journal of Chemical Education, Fruit Anthocyanins: Colorful Sensors of Molecular Milieu, Robert D. Cutright et al., 1994, vol. 71, No. 8, pp. 682-684; and Business Briefing: Innovative Food Ingredients 2002, Applications of Acylated Anthocyanins as Natural Food Colorants, M. Monica Giusti, pp. 1-5.

U.S. Appl. No. 11/557,782, filed Nov. 8, 2006, Luu et al.

Supplementary European Search Report; Application No. EP07754083; date of completion of the search: Nov. 7, 2012; Applicant/Proprietor: Georgia-Pacific Consumer Products LP.

* cited by examiner

ANTI-MICROBIAL HAND TOWEL WITH TIME-DELAY CHROMATIC TRANSFER INDICATOR AND ABSORBENCY RATE DELAY

CLAIM FOR PRIORITY

This application is based upon U.S. Provisional Patent Application Ser. No. 60/786,819, filed Mar. 28, 2006, of the same title. The priority of U.S. Patent Application Ser. No. 60/786,819 is hereby claimed and the disclosure thereof incorporated into this application by reference.

TECHNICAL FIELD

The present invention relates to paper towels used as hand towels. In a preferred embodiment the present invention is directed to an anti-microbial hand towel with a time-delay chromatic transfer indicator which undergoes a visually perceptible color change at a predetermined time after the towel is wetted with, wet hands, for example. An anti-microbial lotion on the towel increases water absorbency times (WAR) to further promote lotion transfer to the skin and increase transfer effectiveness.

BACKGROUND

Frequent hand washing is a simple and effective means to ensure proper hygiene and prevent contamination of food and the spread of disease. Complex systems have been proposed to encourage food service and health care workers to adequately cleanse their hands frequently, in view of the relatively high potential for undesirable contamination associated with their activities.

Washing of the skin, especially the hands, with anti-microbial soap formulations can remove many viruses and bacteria from the washed surfaces. Removal of the viruses and bacteria is due to the surfactancy of the soap and the mechanical action of the wash procedure. Therefore, it is known and recommended that the people wash frequently to reduce the spread of viruses and bacteria. Recent surveys, however, have revealed that while nearly 95% of people claim to have washed their hands after use of public restrooms, actual observations reveal that this figure does not exceed about 66%. Notwithstanding increased awareness, there is a tendency to rush the hand washing process which leads to inadequate hygiene. A number systems and devices to encourage longer and more thorough hand washing have accordingly been developed.

Collopy in U.S. Pat. No. 6,832,916 discloses a hand-washing device containing a display panel that encourages the user to wash their hands for about 15 seconds to remove germs. Gorra, U.S. Pat. No. 5,945,910 discloses method and apparatus for monitoring and reporting hand washing, which includes a sensor for signaling the dispensation of a cleaning agent from a dispenser, and a reporting and monitoring module. Allen et al., U.S. Pat. No. 5,781,942 discloses wash stations and method of operation, which monitors hand washing and assists in hand washing. These systems are relatively expensive and difficult to implement; oftentimes involving training and monitoring personnel. Even when such steps have been taken, there is little certainty that all personnel have followed proper washing procedures.

Frequent hand washing has the drawback that harsh soaps and cleansing agents can irritate the skin and damage the acid mantle of the skin.

Cellulosic substrates coated with lotions are well known in the art. For example, U.S. Pat. No. 5,665,426 to Krzysik et al., is directed towards a lotion formula that can be applied to a tissue, which transfers the lotion to the user's skin in order to reduce irritation and redness. U.S. Pat. No. 5,871,763 to Luu et al., as well is directed towards a lotion formula that is applied to a substrate for skin care treatment. The lotion composition of '763 is melted by the heat produced by the hands of a user of the cellulosic substrate to enable the lotion's transfer to the user's skin. Another lotion-treated substrate is described in U.S. Pat. No. 5,525,345 to Warner et al. The lotion composition of '345 comprises a plastic or fluid emollient that is solid or semi solid at room temperature and an immobilizing agent with a melting point above room temperature, which stabilizes the lotion composition on the surface of the substrate. See also U.S. application Ser. No. 10/483,633 (Publication No. US 2005/0031847), where two separate and distinct phases, lipid and aqueous, are applied to a substrate to facilitate cleansing of skin. Further, there is described in U.S. Pat. No. 4,987,632 to Rowe et al., a cleaning wipe treated with a composition containing detergent, which is leached out upon contact with water.

There are also known lotions containing anti-microbial and pH balancing agents to protect the skin. For example, U.S. Pat. No. 6,238,682 to Klofta et al. is directed towards a tissue treated with anhydrous skin lotion containing anti-microbial components in addition to hydrophilic solvents and surfactants. See also U.S. Pat. No. 6,352,700 to Luu et al., which is directed towards a substrate treated with a lotion that contains a skin pH balancing compound for maintaining a proper skin acid mantle. Other lotions containing anti-microbial agents include U.S. patent application Ser. No. 10/608,661 (Publication No. US 2004/0039353), which is directed towards wet wipes containing a Yucca species extract as an anti-microbial agent; U.S. patent application Ser. No. 09/851,273 (Publication No. US 2002/0031486), which is directed towards an anti-microbial cleansing composition, containing little or no volatile alcohol, that may be used alone or in combination with lotions and the like; U.S. Pat. No. 6,436,885 to Biedermann et al., which is directed towards an anti-microbial cleansing compositions that has a pH of from about 2 to about 5.5; U.S. Pat. No. 6,383,505 to Kaiser et al. which is directed towards an anti-microbial lotion for topical use in a form of oil-in-water emulsion; additionally, similar subject matter is disclosed in U.S. Pat. No. 6,482,423 to Beerse et al.; U.S. Pat. No. 6,488,943 to Beerse et al.; U.S. Pat. No. 6,284,259 to Beerse et al.; U.S. Pat. No. 6,258,368 to Beerse et al.; U.S. Pat. No. 6,183,763 to Beerse et al.; and U.S. Pat. No. 6,210,695 to Beerse et al., as well.

Color indicators are known, for example, to indicate degree of wetness. For example, U.S. patent application Ser. No. 10/806,711 (Publication No. US 2004/0191118) is directed towards a single/multi-layer microporous composite material, containing dispersed pH-sensitive component, which can be embedded in food packaging or diapers to indicate high moisture concentration. The components of the composite material are selected to target specific fluids and regulate their diffusion rate. A single layer composite containing 4% pH indicating agent and 25% fluid regulating additive (to increase diffusion rate) may change its color in less than 30 seconds. Some other wetness indicators specifically address wearable articles such as diapers. Note, for example U.S. Pat. No. 6,904,865 to Klofta et al.; U.S. Pat. No. 6,949,089 to Olson et al.; U.S. Pat. No. 5,690,624 to Sasaki et al.; U.S. Pat. No. 4,705,513 to Sheldon et al.; as well as U.S. Pat. No. 4,231,370 to Mroz et al. U.S. patent application Ser. No. 10/134,207 (Publication No. US 2003/0206940) is directed towards a cosmetic mixture containing a benefit agent and a color dye that are applied to a disposable personal care item. Saturation of the personal care item with water foams the cosmetic mixture and enables its application to skin or hair. Fading of the color dye from the personal care item indicates reduced concentration of the cosmetic mixture in the personal care item and its transfer into the skin or hair of the user. Another example is U.S. Pat. No. 6,733,766 to Gott et al., which is directed towards a personal care composition containing a hydrophobic carrier and hydrophilic colorant, which becomes visually perceivable upon contact with water. U.S. Pat. No. 6,309,655 to Minnix is directed towards a cosmetic anhydrous composition that upon contact with wet skin generates heat, which disintegrates or dissolves granules, embedded within the composition; the granules release a color dye to indicate to the user optimal degree of mixing between the water and the composition. U.S. Pat. No. 6,270,783 to Slavtcheff et al. is directed towards a cosmetic composition, containing a thermochromic substance and exothermic or endothermic agent, which reacts with moisture within the skin to generate heat, and subsequently, change the color of the composition. U.S. Pat. No. 6,007,797 to Bell et al. is directed towards a color sunscreen composition that includes at least one oil soluble dye, which is dissipated as the sunscreen is rubbed into the skin. U.S. Pat. No. 4,029,598 to Neisius et al. is directed towards a pH sensitive indicator azo-dyes used in connection with cellulose or other carriers.

The following are also of interest with respect to active graphics on disposable products: U.S. Pat. No. 6,307,119 to Cammata et al.; U.S. Pat. No. 6,297,424 to Olsen et al. and U.S. patent application Ser. No. 11/043,571 (Publication No. US 2005/0160543).

Despite plentiful art, there exists a need for simple and effective means for promoting hygiene and skin care concurrently in connection with hand washing. The present invention provides a disposable paper towel with an anti-microbial skin care lotion and transfer indicator responsive to a pH balancing agent to promote effective transfer of the lotion to the skin.

SUMMARY OF THE INVENTION

Generally speaking, the present invention provides lotioned towel which provides skin care and anti-microbial activity. Numerous attributes make the lotioned towels of the invention especially suitable for towels used by healthcare and food service workers. In one preferred embodiment, a pH balancing agent and pH sensitive transfer indicator are selected and applied to the web such that a pH sensitive transfer indicator undergoes a gradual color change as the towel is used.

Another aspect of the invention involves increased WAR times. This latter feature, while usually undesirable in a towel product, promotes anti-microbial lotion transfer to the skin as well, since a user will rub the towel longer when drying his or her hands. Accordingly, more recycle fiber in the product can actually be beneficial to the product's performance due to the associated increase in absorption time commonly seen with increased levels of recycle fiber. Lotion transfer is extremely important for both skin care and anti-microbial effectiveness as will be appreciated by one of skill in the art.

Further aspects of the invention are enumerated below and discussed in detail in connection with the various Figures and examples hereinafter provided.

There is provided in a first aspect of the invention an anti-microbial paper towel with a chromatic transfer indicator including a cellulosic web; a transferable lotion composition comprising an emollient and anti-microbial agent, the lotion composition being immobilized on the cellulosic web in a semi-solid or solid form. The transferable lotion composition is selected from lotion compositions which are transferable upon contact with water or lotion compositions which are transferable upon application of heat. There is further provided a water soluble pH balancing agent disposed on the web and a pH-sensitive transfer indicator disposed on the web. The pH-sensitive transfer indicator is chromatically responsive to the pH balancing agent in aqueous form. The pH balancing agent and pH-sensitive transfer indicator are selected and applied to the web such that the pH-sensitive transfer indicator undergoes a gradual color change upon contact with water. Generally, the lotion composition includes from about 0.01 percent by weight to about 10 percent by weight of an anti-microbial agent; more typically the lotion composition comprises from about 0.05 percent by weight to about 5 percent by weight anti-microbial agent. Suitable anti-microbial agents are selected from: 2,4,4'-trichloro-2'-hydroxydiphenyl ether (triclosan); 3,4,4'-trichlorocarbanilide (triclocarban); 3,4,4'-trifluoromethyl-4,4'-d-ichlorocarbanilide (cloflucarban); 5-chloro-2-methyl-4-isothiazolin-3-one; iodopropynl-butylcarbamate; 8-hydroxyquinoline; 8-hydroxyquinoline citrate; 8-hydroxyquinoline sulfate; 4-chloro-3,5-xylenol (chloroxylenol); 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; chlorhexidine gluconate; miconazole; terconazole; butylparaben; ethylparaben; methylparaben; methylchloroisothiazoline; methylisothiazoline; a mixture of 1,3-bis(hydroxymethyl)-5,5-dimethylhydantoin and 3-iodo-2-propynyl butyl carbamate; oxyquinoline; EDTA; tetrasodium EDTA; p-hydroxyl benzoic acid ester; alkyl pyridinum compounds; coco phosphatidyl PG-dimonium chloride; chlorhexidene digluconate; chlorhexidene acetate; chlorhexidene isethionate; chlorhexidene hydrochloride; benzalkonium chloride; benzethonium chloride; polyhexamethylene biguanide; and mixtures thereof. So also, the anti-microbial agent may include a zinc salt.

The pH balancing agent typically includes an organic acid and optionally includes an organic acid/buffer combination such as citric acid and disodium phosphate. Another suitable buffer combination may include disodium citrate and sodium hydroxide. The pH balancing agent is generally applied to the web in an amount of from about 0.5 percent by weight to about 3 percent by weight of the lotion composition. More typically the pH balancing agent is applied to the web in an amount of from about 1 percent by weight to about 2 percent by weight of the lotion composition. The pH balancing agent may include an alpha hydroxy acid, an alpha di-hydroxy acid, a beta hydroxy acid or combinations thereof.

Suitable pH balancing agents are selected from: glycolic acid, alpha-acetyl glycolic acid, lactic acid, tartaric acid, alpha-acetyl lactic acid, alpha-hydroxy isobutyric acid, salicylic acid, mandelic acid, ortho-acetyl mandelic acid, benzilic acid, ortho-acetyl benzilic acid, malic acid, citric acid, gluconic acid, pyruvic acid, sorbic acid and combinations thereof.

The pH-sensitive transfer indicator may include thymol blue, bromo cresol purple, methyl red, cresol red, phenolphthalein, thymolphthalein, or Alizarin yellow R. The pH balancing agent is applied to the web at a plurality of discreet pH balancing agent locations, whereas the pH-sensitive transfer indicator is applied to the web apart from the plurality of discreet pH balancing agent locations. Generally, the pH-sensitive transfer indicator is applied to the web at a plurality of discreet indicator locations whereas the pH balancing agent is applied to the web apart from the plurality of discreet indicator locations.

Preferably the cellulosic web employed in connection with the invention is predominantly softwood fiber and/or recycle fiber and includes a wet strength agent. Suitable wet strength agents may be selected from: aldehyde-containing polyols; aldehyde-containing cationic starch; glyoxal; glutaraldehyde; dialdehydes boric acid carbonate; zirconium ammonium carbonate; glyoxalated polyacrylamide; polyamide-epichlorohydrin; polyamine-epichlorohydrin; urea-formaldehyde; melamine-formaldehyde; polyethyleneimine; and latex emulsions.

In another aspect of the invention there is provided a water soluble triggering agent on the web and a pH-sensitive transfer indicator which are selected and applied such that the pH-sensitive transfer indicator undergoes a visually perceivable color change upon contact with water after a characteristic time delay of at least about 5 seconds. A time delay of at least about 10 seconds, 15 seconds or 20 seconds is preferred in some cases.

In another aspect of the invention the transferable lotion is a lotion emulsion including an anti-microbial agent disposed on the web, the lotion emulsion including a polar emollient and a non-polar emollient as well as a surfactant composition comprising a non-ionic surfactant. The lotion emulsion is substantially liquid at room temperature; however, the emollients and surfactant composition are selected such that the lotion emulsion is immobilized on the web in a semi-solid or solid state when applied thereto. The lotion emulsion is preferably capable of forming an aqueous gel upon contact with water. The lotion emulsion includes a polar emollient in an amount of from about 2 percent by weight of the lotion emulsion to about 40 percent by weight of the lotion emulsion. The lotion emulsion may include a poly-hydroxy emollient selected from: propylene glycol; glycol; glycerol; diethylene glycol; methylene glycol; polypropylene glycol; polyethylene glycol and sorbitol. Further, the lotion emulsion may include a non-polar emollient in an amount of from abut 10 percent by weight of the lotion emulsion to about 40 percent by weight of the lotion emulsion. Suitable non-polar emollients may be selected from: aromatic or linear esters; Guerbet ester; mineral oil; squalane; liquid paraffin, and mixtures thereof. Particular non-polar emollients which are suitable include isopropyl myristate and $C_{12}$-$C_{15}$ alkyl benzoate ester (Finsolv TN). Other suitable non-polar emollients are tri-octyldodecyl-citrate and a mixture of $C_{12}$-$C_{15}$ alkyl benzoate ester and carnation oil.

The surfactant composition may include a non-ionic surfactant and fatty alcohol in the amount of from about 40 percent by weight to about 70 percent by weight of the lotion emulsion. Suitable non-ionic surfactants include: PEG-20 methyl glucose sesquistearate; PPG-20 methyl glucose ether; PPG-20 methyl glucose ether distearate; PEG-20 methyl glucose distearate; PEG-120 methyl glucose dioleate; ethoxylated methyl glucose having from about 10 to about 20 repeating ethoxy units per molecule, a mixture thereof and the like.

In a preferred embodiment the surfactant composition comprises a co-surfactant in the amount of from about 0.1 percent to about 20 percent by weight of the lotion emulsion. The co-surfactant is suitably selected from $C_{12}$-$C_{18}$ fatty alcohols, behenyl alcohol, cetyl alcohol, stearyl alcohol, iso-cetyl alcohol, and iso-stearyl alcohol and mixtures thereof. One preferred co-surfactant is a mixture of cetyl alcohol and stearyl alcohol. Perhaps most preferably, the micro-emulsion is substantially waterless and capable of forming an aqueous micro-emulsion when mixed with water as will be appreciated from the examples appearing hereinafter.

Instead of a lotion emulsion, anti-microbial lotion may be applied in heat sensitive form in another aspect of the invention. In such cases, the transferable lotion disposed on the web includes an emollient, an anti-microbial agent, and a retention/release agent such that the lotion has a ΔH above about 37° C. of more than 10 calories/gram, a total heat of melting of above about 25 calories/gram, and an onset of melting temperature of at least about 30° C. The lotion may further include a surfactant composition in the amount of from about 10 percent to about 15 percent by weight of the lotion composition. The surfactant may be selected from methyl glucoside sesquistearate, ethoxylated methyl glucoside sesquistearate containing 20 moles of oxyethylene units, or combinations thereof. A preferred surfactant is a mixture of PEG-20 methyl glucose sesquistearate (Glucamate SSE-20) and methyl glucose sesquistearate (Glucate SS). In connection with heat transferable lotions, the lotion composition may include an emollient in the amount of from about 5 percent to about 75 percent by weight of the lotion composition. The emollient may include an aromatic ester emollient, a fatty alcohol ester of a non-fatty organic acid emollient, or mixtures thereof. Suitable aromatic ester emollients include benzoate ester emollients, selected from $C_{12}$-$C_{15}$ alkyl benzoate, stearyl benzoate, octyl dodecyl benzoate, isostearyl benzoate, methyl gluceth-20 benzoate, stearyl ester benzoate, poloxamer 182 dibenzoate, poloxamer 105 benzoate, or mixtures thereof. Likewise, fatty alcohol esters of a non-fatty organic acid emollient includes $C_{12}$-$C_{15}$ octanoate, for example. Heat sensitive lotions preferably include a retention/release agent in an amount of from about 25 percent to about 95 percent by weight of the lotion composition. Suitable retention/release agents include $C_{12}$-$C_{18}$ fatty alcohols. Fatty alcohols may be selected from dodecanol, tridecanol, tetradecanol, pentadecanol, hexadecanol, heptadecanol, octadecanol, or mixtures thereof. One preferred retention/release agent is a mixture of cetyl alcohol and stearyl alcohol. Here again, the lotion composition is preferably substantially waterless.

In another aspect of the invention, the transferable lotion composition disposed on the web is selected and applied to the web in amounts such that the lotion imparts a water absorption rate delay of at least about 25 percent. A water absorption rate delay of at least 50 percent is typical. There may be a water absorption rate delay of at least about 75 percent or 100 percent imparted to the cellulosic web as will be appreciated from the examples which follow.

While the products of the invention exhibit a substantial absorption rate delay, the SAT value of the lotion product is substantially the same as the unlotioned cellulosic web from which the towel is made. Generally, products of the invention have a SAT value of from about 2 g/g to about 5 g/g. A SAT value of at least about 3 g/g is preferred as are values of 3.5 g/g, 4 g/g, and 4.5 g/g in some embodiments.

The lotioned products of the invention generally exhibit a WAR value of at least about 40 seconds and in some cases at least about 50 seconds. Typical products have WAR values of from about 55 to about 75 seconds. WAR values of at least about 100 seconds or at least about 120 seconds may likewise be observed; especially in products comprising large amounts of recycle fiber where reduced rates of absorption are beneficial to product performance. WAR values of from about 75 seconds to about 200 seconds are desirable in some cases.

The transferable lotion of the invention is generally applied to the cellulosic web in an amount of from about 3 percent to about 20 percent by weight, based on the combined weight of the dry web and the lotion. From about 5 percent by weight to about 15 percent by weight is typical and from about 8 percent by weight to about 10 percent by weight is preferred in some cases.

The towel of the invention generally has a basis weight of about 15 to about 65 g/m$^2$; typically of from about 25 to about 50 g/m$^2$ and preferably from about 30 to about 40 g/m$^2$. As noted above, the towel is preferably made with fiber consisting predominantly of softwood and/or recycle fiber. Typically the web is greater than about 65 percent by weight softwood and/or recycle fiber and preferably at least about 70 percent by weight softwood and/or recycle fiber. Softwood and/or recycle fiber content of from about 70 to about 90 percent by weight based on the dry fiber in the furnish is generally preferred. In some embodiments, it is desirable to have at least 50% by weight of fiber recycle fiber. At least 60%, at least 70%, at least 80% or at least 90% by weight of recycle fiber may be preferred in still other cases. In one preferred embodiment, the fiber in the web is 100% by weight recycle fiber. Recycle fiber may be added to the finish in any amount. While any suitable recycle fiber may be used, recycle fiber with relatively low levels of groundwood is preferred in many cases, for example recycle fiber with less than 15% by weight lignin content, or less than 10% by weight lignin content may be preferred depending on the furnish mixture employed and the application.

An especially preferred softwood fiber is Douglas fir fiber. The anti-microbial sheet of the invention may be in the form of a single ply towel having an eight sheet caliper of from about 35 to about 90 mils.

In another aspect of the invention, there is provided an anti-microbial paper towel with a chromatic transfer indicator including: a) a cellulosic web; b) a transferable lotion composition comprising an emollient and anti-microbial agent, the lotion composition being immobilized on the cellulosic web in a semi-solid or solid form, wherein the transferable lotion composition is selected from lotion compositions which are transferable upon contact with water or lotion compositions which are transferable upon application of heat and is applied to the towel at an add-on of from about 3 to about 20 weight percent; and c) a chromatic transfer indicator which fades after a characteristic time delay of at least about 5 seconds after contact with the water. In one preferred embodiment, the transfer indicator comprises a water-soluble polymer which may be selected from the group consisting of polyvinyl alcohol, starch, oxygenated hydrocarbons, polyacrylic acid, dextrin, and hydroxypropyl cellulose; alternatively, the transfer indicator comprises a surfactant. The towel may have an unlotioned basis weight generally of from about 15 lbs. per 3000 square foot ream to about 45 lbs. per 3000 square feet ream. An unlotioned basis weight of from about 20 lbs. per 3000 square foot ream to about 40 lbs. for 3000 square foot ream is more typical, with an unlotioned basis weight of from about 25 lbs. per 3000 square foot ream to about 35 lbs. per 3000 square foot ream being preferred in many cases. The transferable lotion is applied to the web at an add-on rate of from about 5 to about 15 weight percent; with from about 8 to about 10 weight percent being somewhat typical.

Further details and aspects of the invention will become apparent from the discussion which follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
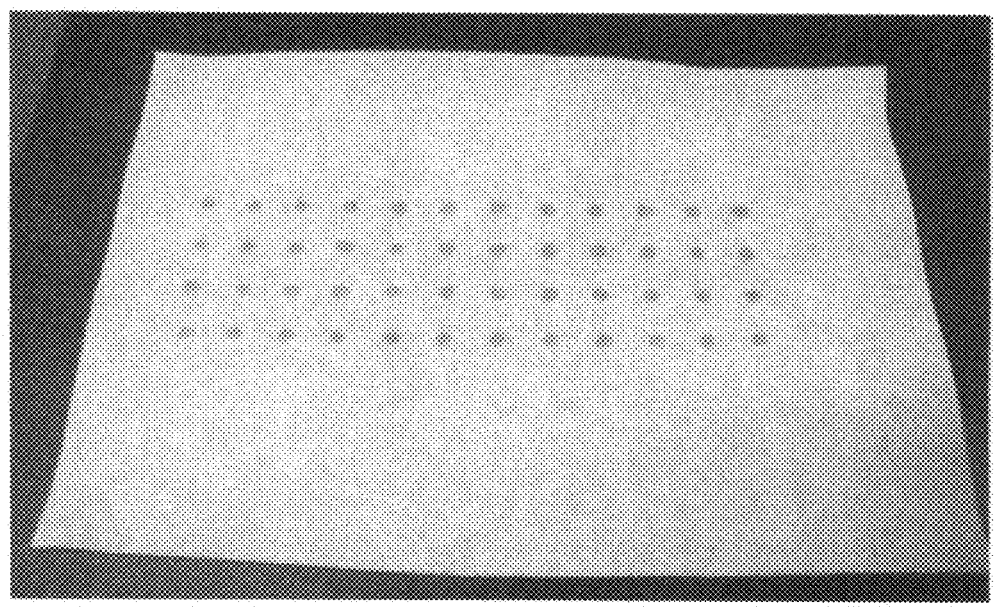
FIGS. 1 and 3 are photographs of an unused paper towel treated with a pH balancing agent (citric acid), and transfer indicator (thymol blue)
Figure 2:
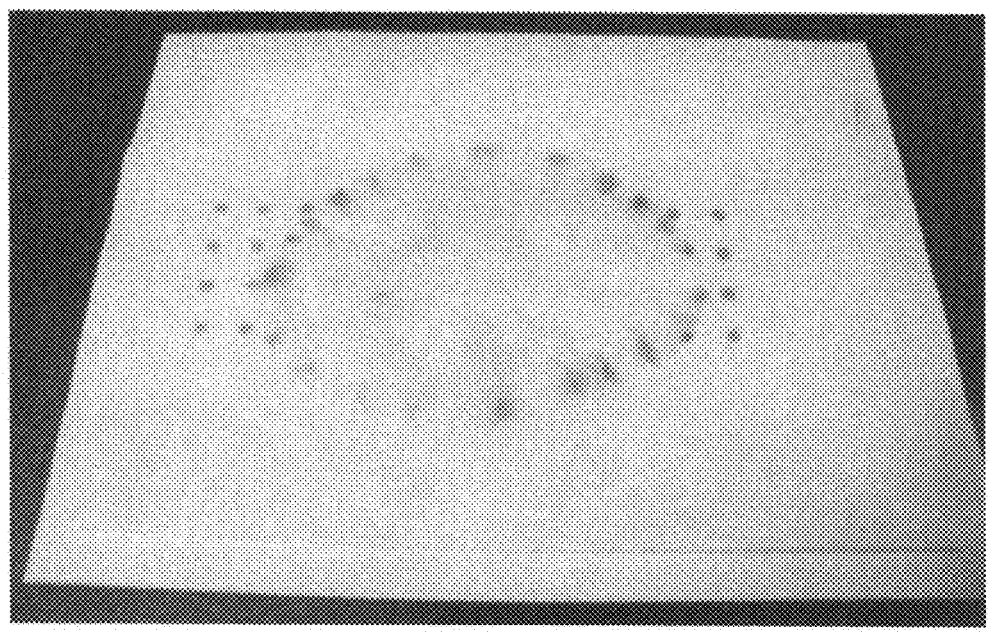
FIGS. 2 and 4 are photographs of a paper towel treated with a pH balancing agent (citric acid), and transfer indicator (thymol blue) after it has been in contact with water.
Figure 3:
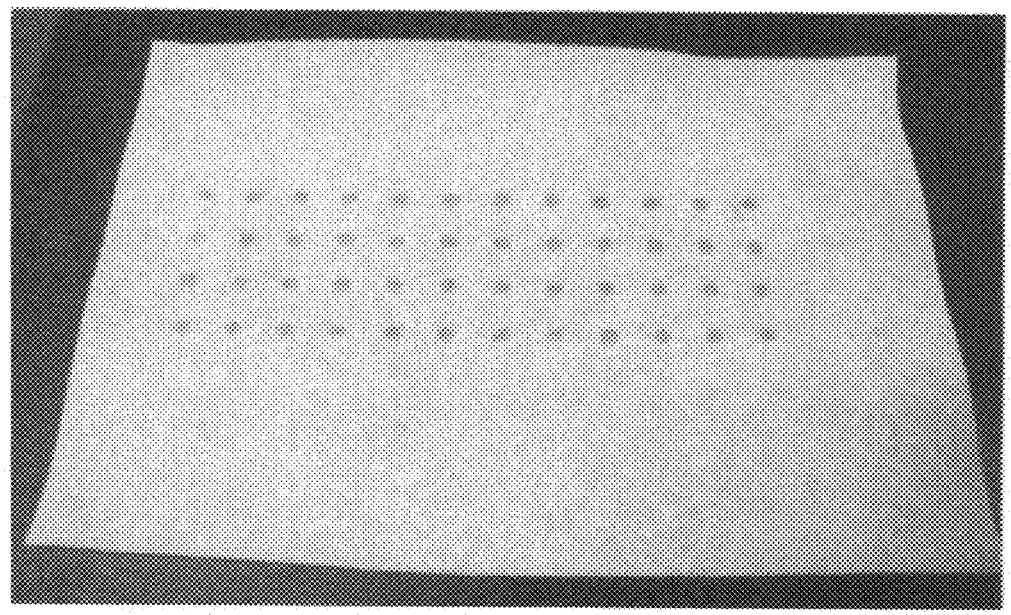
Figure 4:
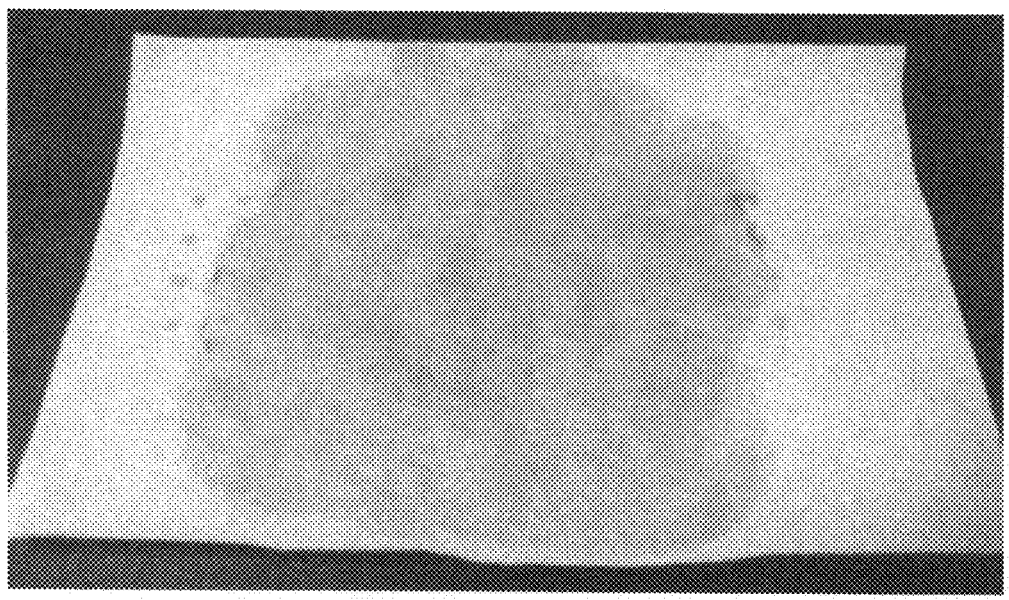

The invention is described in detail below for purposes of illustration only. Modifications within the spirit and scope of the invention, set forth in the appended claims, will be readily apparent to one of skill in the art. As used herein, terminology and abbreviations have their ordinary meaning; for example, "cps" refers to centipoises; g refers to grams, mg refers to milligrams, m$^2$ refers to square meters and so forth.

Absorbency of the inventive product is measured with a simple absorbency tester. The simple absorbency tester is a particularly useful apparatus for measuring the hydrophilicity and absorbency properties of a sample of tissue, napkin, or towel. In this test a sample of tissue, napkin, or towel 2.0 inches in diameter is mounted between a top flat plastic cover and a bottom grooved sample plate. The tissue, napkin, or towel sample disc is held in place by a ⅛ inch wide circumference flange area. The sample is not compressed by the holder. De-ionized water at 73° F. is introduced to the sample at the center of the bottom sample plate through a 1 mm. diameter conduit. This water is at a hydrostatic head of minus 5 mm. Flow is initiated by a pulse introduced at the start of the measurement by the instrument mechanism. Water is thus imbibed by the tissue, napkin, or towel sample from this central entrance point radially outward by capillary action. When the rate of water imbibation decreases below 0.005 gm water per 5 seconds, the test is terminated. The amount of water removed from the reservoir and absorbed by the sample is weighed and reported as grams of water per square meter of sample or grams of water per gram of sheet. In practice, an M/K Systems Inc. Gravimetric Absorbency Testing System is used. This is a commercial system obtainable from M/K Systems Inc., 12 Garden Street, Danvers, Mass., 01923. WAC or water absorbent capacity also referred to as SAT is actually determined by the instrument itself. WAC is defined as the point where the weight versus time graph has a "zero" slope, i.e., the sample has stopped absorbing. The termination criteria for a test are expressed in maximum change in water weight absorbed over a fixed time period. This is basically an estimate of zero slope on the weight versus time graph. The program uses a change of 0.005 g over a 5 second time interval as termination criteria; unless "Slow SAT" is specified in which case the cut off criteria is 1 mg in 20 seconds.

Water absorbency rate or WAR, is measured in seconds and is the time it takes for a sample to absorb a 0.1 gram droplet of water disposed on its surface by way of an automated syringe. The test specimens are preferably conditioned at 23° C.±1° C. (73.4±1.8° F.) at 50% relative humidity. For each sample, 4 3×3 inch test specimens are prepared. Each specimen is placed in a sample holder such that a high intensity lamp is directed toward the specimen. 0.1 ml of water is deposited on the specimen surface and a stop watch is started. When the water is absorbed, as indicated by lack of further reflection of light from the drop, the stopwatch is stopped and the time recorded to the nearest 0.1 seconds. The procedure is repeated for each specimen and the results averaged for the sample. WAR is measured in accordance with TAPPI method T-432 om-99.

The water absorption rate delay in percent is calculated from the WAR values of the unlotioned cellulosic web and lotioned sheet product of the invention as follows:

Absorption rate delay=(WAR value of lotioned cellulosic sheet−WAR value of unlotioned cellulosic web)÷(WAR value of unlotioned cellulosic web)×100%

"Aqueous gel" refers to viscous lotion/water compositions typically having a room temperature viscosity of above about 500 cps at room temperature and typically above about 1000 cps at room temperature. Preferred lotion compositions form gels of more than 1500 cps at room temperature as is seen in Table 2 below.

"Basis weight", BWT, bwt and so forth is expressed in grams per square meter or pounds per 3000 square foot ream of product as is indicated.

The term "cellulosic", "cellulosic sheet" and the like is meant to include any product incorporating papermaking fiber having cellulose as a major constituent. "Papermaking fibers" include virgin pulps or recycle (secondary) cellulosic fibers or fiber mixes comprising cellulosic fibers. Fibers suitable for making the webs of this invention include fibers such as those obtained from deciduous and coniferous trees, including softwood fibers, such as northern and southern softwood kraft fibers; hardwood fibers, such as eucalyptus, maple, birch, aspen, or the like as well as nonwood cellulosic fibers. Papermaking fibers can be liberated from their source material by any one of a number of chemical pulping processes familiar to one experienced in the art including sulfate, sulfite, polysulfide, soda pulping, etc. The pulp can be bleached if desired by chemical means including the use of chlorine, chlorine dioxide, oxygen, alkaline peroxide and so forth. The products of the present invention may comprise a blend of conventional fibers (whether derived from virgin pulp or recycle sources) and high coarseness lignin-rich tubular fibers, such as bleached chemical thermomechanical pulp (BCTMP). "Furnishes" and like terminology refers to aqueous compositions including papermaking fibers, optionally wet strength resins, debonders and the like for making paper products.

Preferably, the fiber in the towel products of the invention consists predominantly (more than 50% by weight of fiber based on fiber content) of softwood (SW) fiber such as Douglas fir. Southern Softwood Kraft (SSWK) is also a preferred fiber. Softwood fibers provide strength to the product; Southern softwoods are generally preferred for towel of the invention; however thin and flexible Northern softwood may be used in some fiber mixtures.

Percent means weight percent unless otherwise indicated and refers to weight percent without water unless the inclusion of the water weight is expressly indicated. Weight percent softwood fiber and like terminology or expressions refer to the weight percent of softwood fiber based on fiber content of a product or composition only, exclusive of other ingredients.

Room temperature refers to a temperature of from about 20° C. to about 25° C.

Characteristic time delay of the transfer signal of a towel product of the invention is determined by placing a sample of towel on the surface of a bath of deionized water (or any source sufficient to saturate the sample) and recording the time delay between placing the towel on the bath (t=0) and a visually observable color change (t=characteristic time delay). Time delay is expressed in seconds.

Dry tensile strengths (MD and CD), stretch, ratios thereof, modulus, break modulus, stress and strain are measured with a standard Instron test device or other suitable elongation tensile tester which may be configured in various ways, typically using 3 or 1 inch wide strips of tissue or towel, conditioned in an atmosphere of 23°±1° C. (73.4°±1° F.) at 50% relative humidity for 2 hours. The tensile test is run at a crosshead speed of 2 in/min. Break modulus is expressed in grams/3 inches/% strain. % strain is dimensionless and need not be specified.

Tensile ratios are simply ratios of the values determined by way of the foregoing methods. Unless otherwise specified, a tensile property is a dry sheet property.

The wet tensile of the tissue of the present invention is measured using a three-inch wide strip of tissue that is folded into a loop, clamped in a special fixture termed a Finch Cup, then immersed in a water. The Finch Cup, which is available from the Thwing-Albert Instrument Company of Philadelphia, Pa., is mounted onto a tensile tester equipped with a 2.0 pound load cell with the flange of the Finch Cup clamped by the tester's lower jaw and the ends of tissue loop clamped into the upper jaw of the tensile tester. The sample is immersed in water that has been adjusted to a pH of 7.0±0.1 and the tensile is tested after a 5 second immersion time.

"Waterless", "substantially waterless" and like terminology refers to compositions which include generally less than about 10% by weight water. In cases where water is present at all, water is preferably not added as such, but is contained in other ingredients.

In some preferred embodiments of the present invention, the lotion composition is a "cold," lotion such as the lotions described in U.S. Pat. No. 7,169,400 to Luu et al., incorporated herein by reference in its entirety. "Cold" lotions refer to lotions that are substantially liquid at room temperature and can be applied as such to substrates. Due to the liquid state of the "cold" lotions at room temperature, they do not require heating or melting equipment and can be applied to the substrates by several available technologies such as spraying, printing, coating, extrusion or other techniques.

The cold lotion used in the present invention contains a micro-emulsion composition containing predominantly an emollient composition and a surfactant composition. The small particle size of the micro-emulsion increases the surface area of its constituents so it contributes to the utility of the present composition in increasing the interaction between the emollient and the skin surface; a desirable property for restoring the oil layer of the skin. Preferably, the micro-emulsion composition contains an external continuous non-polar or polar emollient, an internal discontinuous polar or non-polar emollient, a surfactant and a mixture of fatty alcohol co-surfactants. The lotion composition may also contain optional ingredients, including typical cosmetic additives, preservatives, plant extracts, fragrances, and medicinal agents. Any suitable combination or proportion of ingredients which produces a micro-emulsion can be used.

Figure 5:
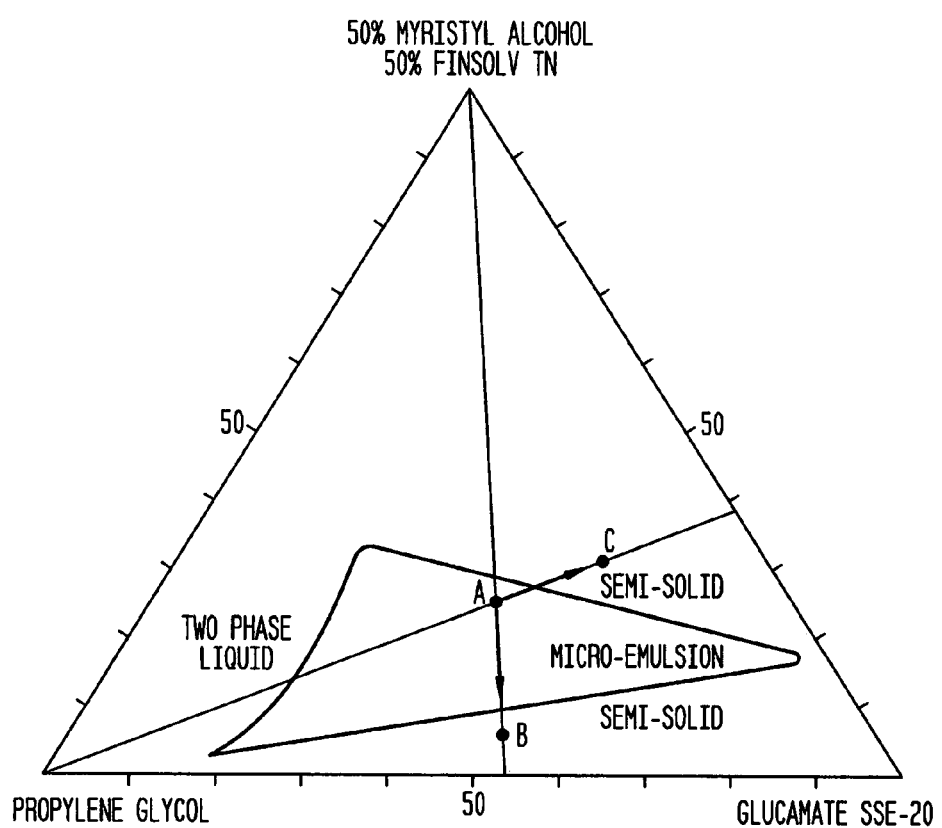
FIG. 5 is a partial phase diagram of the composition of Example 2 showing the phase characteristics of a waterless micro-emulsion.

An important aspect of the cold lotion employed is when the liquid lotion contacts the fibers or non-woven substrate, it undergoes an in-situ phase change from liquid to immobilized semi-solid or solid form. This phase change of the lotion results when the substrate web surface fibers absorb the continuous outer phase of the micro-emulsion, which may be a non-polar or polar-emollient. Subsequently, the percent of the outer phase of the micro-emulsion within the composition is reduced, resulting in increase in the percent of the internal phase of the micro-emulsion and shuft of the original lotion composition from point A (liquid micro-emulsion) to points B or C (semi-solid state), which are located outside of the micro emulsion region (see FIG. 5). The immobilized antimicrobial lotion is restorable to transferable form upon contact with water and is capable of forming an aqueous gel. The compositions of the present invention are preferably chosen to lie within the micro-emulsion region of a given formulation. All percentages, ratios, and proportions of the ingredients within the compositions of the present invention are determined by the micro-emulsion region of a ternary phase diagram of the polar emollient/non-polar emollient/co-surfactant/non-ionic surfactant formulations (PE/NPE/COS/NIS). Outside of the micro-emulsion region on the low percent side of the polar or non-polar emollients, a semi-solid or solid region is preferably present. A micro-emulsion is thermodynamically stable and is essentially transparent in the visible region of the spectrum, which typically indicates that particle size diameter is preferably less than about 0.1 micron, or so. When the particle size diameter is greater than about 3,200 A (about 0.32 micron), the liquid is no longer considered a micro-emulsion but is an emulsion which can often appear turbid and be thermodynamically unstable. The micelle structure of a micro-emulsion is either a "direct" type (head out/tail in) or an "inverse" type (head in/tail out). The liquid micro-emulsion increases the surface area of the lipophilic constituent so it contributes significantly to the utility of the present composition in neat form. Fluidity on the skin surface, small particle size, high surface area and high hydrophilic character, are highly desirable properties for cleansing purposes either when the substrate is used by itself or when lotioned products are rewet with water. Any combination or proportion of these ingredients which produces a micro-emulsion can be used.

A hot lotion composition used in connection with the present invention is chosen such that its ΔH of above about 37° C. is above about 10 calories/gram, ΔH of below about 37° C. is above about 15 calories/gram, ΔH total (total energy to melt) of above about 37° C. is above about 25 calories/gram. Further, the retention/release agent is preferably selected to have a melting point substantially higher than about room temperature but lower than about 65° C., such that the lotion onset of melting temperature is within the range of from about 30° C. to about 45° C. This enables the lotion composition to maintain a substantially solid state at about room temperature and partially melted state at human skin temperature.

It should be noted that for purposes of this description, the temperature of human skin is between about 30° C. to about 37° C. and room temperature is between about 20° C. to about 25° C.

An important aspect of a hot lotion used is that it is partially melted by body heat to enable transfer to the skin of partially liquefied and partially solid emollient(s), particles of retention/release agent and other ingredients. The partial melting of the lotion is important, because when the lotion is completely melted to liquid by body heat it is perceived as too greasy, and when a lotion is not sufficiently melted by body heat, it would not spread easily on the skin. At least a portion of the partially melted lotion resolidifies on the skin to form a smooth and moisturizing layer. Further details as to suitable hot lotion compositions are found in U.S. Pat. No. 5,871,763, the disclosure of which is incorporated herein by reference in its entirety.

Optionally included in the anti-microbial lotions are suitable anti-viral agents including those effective against, or at least retardant toward Corona virus, Picorna virus, Rhino virus, Herpes simplex, Herpes genitalis, Herpes labialis, Respiratory Syncytial Virus (RSV), Para influenza, Cytomegalovirus, Adenovirus, Condyloma and certain synergistic disease states that can involve a virus and a protozoa or a virus and any unfriendly enzymes, e.g., protease, lipase and amylase, that cause a compromised skin as a precursor state for a viral infection to occur. Specific anti-viral agents suitable for use in the lotions include bioflavonoids such as hesperitin, naringin, catechin and certain selected amino acids of leguminous origin such as L-canavanine and an analog of L-arginine; dicarboxylic acids such as malonic, glutaric, citric, succinic, and diglycolic acids; alpha hydroxy carboxylic acid such as D-galacturonic acid from Sterculia urens; neem seed oil (Azadirachta indica) in its un-denatured form; sandalwood oil (Santalum album L.) in its un-denatured form. Optionally, the anti-viral agent could be admixed with at most about 50% by weight of the anti-viral agent of a protease inhibitor such as zinc oxide or other suitable zinc salt.

The cold or hot lotion composition can include other optional components typically present in lotions of this type. These optional components include a botanical extract, such as aloe extract, avocado oil, basil extract, sesame oil, olive oil, jojoba oil, chamomile extract, eucalyptus extract, peppermint extract, as well as animal oils such as emu oil, cod liver oil, orange roughy oil, mink oil, and the like.

The lotion of the present invention can also optionally include a humectant. Humectants are hygroscopic materials with a two-fold moisturizing action including water retention and water absorption. Humectants prevent the loss of moisture from skin and help to attract moisture from the environment. Preferred humectants include glycerol, hydrolyzed silk, ammonium lactate, hydroxypropyltrimonium hydrolyzed silk, hydroxypropyl chitosan, hydroxypropyltrimonium hydrolyzed wheat protein, lactamidopropyltrimonium chloride, and ethyl ester of hydrolyzed silk. The botanical extract, animal oil or humectant is preferably present in an amount of less than about 3% when used in the base formulation of the lotion. Further optional components include a skin refreshing agent such as encapsulated water in oil, eucalyptus oil, and menthol oil. All of these optional materials are well known in the art as additives for such formulations and can be employed in appropriate amounts in the lotion compositions of the present invention by those skilled in the art.

The lotion can optionally include a fragrance. The fragrance can be present in an amount of from 0.01% to about 2%. Suitable fragrance includes volatile aromatic esters, non-aromatic esters, aromatic aldehydes, non-aromatic aldehydes, aromatic alcohols, non-aromatic alcohols, heterocyclic aroma chemicals, and natural floral fragrances, such as blossom, carnation, gardenia, geranium, iris, hawthorne, hyacinth and jasmine.

The lotion can also optionally include natural or synthetic powder like talc, mica, boron nitride, silicone, or mixtures thereof.

The towel web of the present invention can be any suitable cellulosic substrate web, optionally wet-strengthened, and optionally including synthetic fibrous material such as melt-blown polyethylene, polypropylene, copolymers of polyethylene. The substrate also may be embossed.

Wet strength agents which may be added include temporary as well as permanent wet strength agents. Suitable wet strength agents include glyoxal; glutaraldehyde; uncharged chemical moieties selected from a group consisting of dialdehydes, aldehyde-containing polyols, uncharged aldehyde-containing polymers, and cyclic ureas and mixtures thereof, and aldehyde-containing cationic starch; mixtures of polyvinyl alcohol and salts of multivalent anions, such as boric acid or zirconium ammonium carbonates; glyoxalated polyacrylamide; polyamide-epichlorohydrin; polyamine-epichlorohydrin; urea-formaldehyde; melamine-formaldehyde; polyethyleneimine; and latex emulsions.

The present invention includes a web of cellulosic fibers treated on at least one side thereof, preferably in an amount of from about 0.1% to about 25%, more preferably from about 0.5% to about 20%, by weight of the dried fiber web with an ant-microbial lotion.

The cellulosic substrate can be prepared according to conventional processes (including TAD, CWP and variants thereof) known to those skilled in the art. In many cases, the fabric creping techniques revealed in the following co-pending applications will be especially suitable: U.S. patent application Ser. No. 11/678,669, entitled "Method of Controlling Adhesive Build-Up on a Yankee Dryer; U.S. patent application Ser. No. 11/451,112 (Publication No. US 2006-0289133), filed Jun. 12, 2006, entitled "Fabric-Creped Sheet for Dispensers"; U.S. Ser. No. 11/451,111, filed Jun. 12, 2006 (Publication No. US 2006-0289134), entitled "Method of Making Fabric-creped Sheet for Dispensers"; U.S. patent application Ser. No. 11/402,609 (Publication No. US 2006-0237154), filed Apr. 12, 2006, entitled "Multi-Ply Paper Towel With Absorbent Core"; U.S. patent application Ser. No. 11/151,761, filed Jun. 14, 2005 (Publication No. US 2005/0279471), entitled "High Solids Fabric-crepe Process for Producing Absorbent Sheet with In-Fabric Drying"; U.S. application Ser. No. 11/108,458, filed Apr. 18, 2005 (Publication No. US 2005-0241787), entitled "Fabric-Crepe and In Fabric Drying Process for Producing Absorbent Sheet"; U.S. application Ser. No. 11/108,375, filed Apr. 18, 2005 (Publication No. US 2005-0217814), entitled "Fabric-crepe/Draw Process for Producing Absorbent Sheet"; U.S. application Ser. No. 11/104,014, filed Apr. 12, 2005 (Publication No. US 2005-0241786), entitled "Wet-Pressed Tissue and Towel Products With Elevated CD Stretch and Low Tensile Ratios Made With a High Solids Fabric-Crepe Process"; U.S. application Ser. No. 10/679,862 (Publication No. US 2004-0238135), filed Oct. 6, 2003, entitled "Fabric-crepe Process for Making Absorbent Sheet"; U.S. Provisional Patent Application Ser. No. 60/903,789, filed Feb. 27, 2007, entitled "Fabric Crepe Process With Prolonged Production Cycle"; U.S. Provisional Patent Application Ser. No. 60/850,467, filed Oct. 10, 2006, entitled "Absorbent Sheet Having Lyocell Microfiber Network"; GP-06-8-1); U.S. Provisional Patent Application Ser. No. 60/808,863, filed May 26, 2006, entitled "Fabric-creped Absorbent Sheet with Variable Local Basis Weight"; and U.S. Provisional Patent Application Ser. No. 60/784,228, filed Mar. 21, 2006, entitled "Absorbent Sheet Having Lyocell Microfiber Network". The applications referred to immediately above are particularly relevant to the selection of machinery, materials, processing conditions and so forth as to fabric creped products of the present invention and the disclosures of these applications are incorporated herein by reference.

The methodology employed for fabric creped substrates includes: a) compactively dewatering a papermaking furnish to form a nascent web having an apparently random distribution of papernaking fiber; b) applying the dewatered web having the apparently random fiber distribution to a translating transfer surface moving at a first speed; and c) fabric-creping the web from the transfer surface at a consistency of from about 30% to about 60%, the creping step occurring under pressure in a fabric creping nip defined between the transfer surface and the creping fabric wherein the fabric is traveling at a second speed slower than the speed of said transfer surface, the fabric pattern, nip parameters, velocity delta and web consistency being selected such that the web is creped from the transfer surface and redistributed on the creping fabric to form a web with an optionally drawable reticulum having a plurality of interconnected regions of different local basis weights including at least (i) a plurality of fiber-enriched regions of high local basis weight, interconnected by way of (ii) a plurality of optionally elongated densified regions of compressed papermaking fibers, the densified regions having relatively low local basis weight and optionally being generally oriented along the machine direction (MD) of the sheet. In one embodiment, the elongated densified regions are further characterized by an MD/CD aspect ratio of at least 1.5.

A preferred towel web is a fabric-creped towel web as is used in Example 18. Lotion can be applied to the substrate according to conventional application methods known to those skilled in the art.

Example 1

Towels of the invention include a time-delay chromatic transfer indicator to help promote lotion transfer to the skin by encouraging prolonged contact with the skin. Typically, the towel includes a transfer indictor system with an invisible part and a visible part which may be applied to a towel with a multi-layer glue applicator utilized in connection with a 3 or 4 roll embossing station. The invisible part of the system (which may be incorporated in a lotion formula) is transferred to the towel, either on a separate sheet for 2-ply product or are side-by-side on the same sheet for a 1-ply product but the "trigger", for example, of organic acid is kept separate from the transfer indicator, that is, the trigger is suitably disposed in a plurality of locations apart from a plurality of locations where the transfer indicator is located.

The color of a visible part of the transfer indicator system should be red, purple, green or blue and contains a pH sensitive material. The pH of these colorants is either acidic (1-5) or basic (7.5-14) and they are either in aqueous solution with or without solvent or encapsulated. The colorants may be either food contact or non-food contact chemicals.

When users of the towel dry their wetted hands, time for disappearance of the "visible part" of the upper indicator system can be an effective tool to communicate to them that the duration of hand rubbing was in a proper manner, about 15 seconds or more as is suitable for the lotion. This encouraged vigorous wiping action, which has been shown to remove further microorganisms and contamination after hand washing, and also to improve transferring lotion active agents to skin. Increasing or decreasing the wicking time and the chemical concentration of the invisible part, as well as from a specific graphic design of the visible part, can control the towel response.

In the attached FIGS. 1 through 4, the system of "thymol blue/citric acid" is printed on a hand towel basesheet. The visible blue dots are thymol blue (pH=8 to 9.5), they are surrounded by the invisible dots of citric acid (pH=2). When the prototype is wetted with city water, the wetted part of the hand towel becomes colorless with or without wiping action.

The enhanced towel of the invention is preferably dispensed in a touchless dispenser or as multifold towel in a hands-free dispenser.

The chromatic transfer indicator is in many preferred cases a fading design or graphic which is provided by any suitable means such as pH sensitive inks, water soluble inks, colored particles, hydratable salts; or another colorant which fades substantially upon contact with tap water. It will be appreciated from the foregoing that the indicator systems preferably includes a visible part and an invisible part as follows:

1) Visible Part: The color of this part should be red, purple, green or blue and contains pH sensitive materials. The pH of these colorants is either acidic (1-5) or basic (7.5-14), and they are either in aqueous solution with or without solvent or encapsulated. Furthermore, these chemicals are either food on non-food contact materials. The colorant of the visible part is printed on the surface of the paper, plastic film, or non-woven substrate with a specific, selected design to demonstrate the benefit of the product. The selected design can be a word, sentence, graphic or special pattern, alone or in combination with an embossing design.

2) Invisible Part: The function of this part, when the product is wetted with water, is providing the necessary pH for changing the visible color to a colorless or a lighter color. The chemical of the invisible part might include non-toxic organic acid (i.e., citric acid, lactic acid, glycolic acid, etc.), inorganic acid or a buffer solution, providing its pH is in the range of 5.5 to 7. The invisible material is usually colorless and water-soluble and printed on the surface of the substrate, either on a separate sheet or side by side on the same sheet but not in contact with the visible material.

The desired time for disappearance of the visible part can be controlled by increasing or decreasing the wicking time of the invisible part by blending it with lotion, hydrophobic or hydrophilic surfactant, or water-soluble polymer such as PVOH, polyacrylic acid, starch, dextrin, hydroxypropyl cellulose, etc. Increasing or decreasing the chemical concentration or the distance between visible and invisible material in the pattern design is also a simple method in providing an appropriate disappearance time of the visible part of the disappearing graphic.

The transfer indicator can be applied on a hand-washing towel, kid's towel, guest towel, etc., and it can also be applied as a Wetting Indicator (WI) for diapers. In the attached FIGS. 1 to 4, the Thymol blue/acid citric system is printed on a hand towel. The visible blue dots are thymol blue (pH=8-9.5); they are surrounded by invisible dots of citric acid (pH=2) of like size and frequency. When the prototype is rewetted with city water (FIGS. 2, 4), the wetting part of the hand towel becomes colorless with or without wiping action. FIGS. 1-4 show that the "thymol blue-citric acid" system as well as the pattern design are the key to contributing to the achievement of the desired wiping time for the use of transferring anti-microbial lotion, for example.

Examples 2-8

Formulations of the waterless lotion were prepared in which, the components, their ratios and the conditions selected to provide micro-emulsion subject to in-situ phase change upon contact with a cellulosic substrate were varied as shown in the following Examples.

In preparing each formulation the following, a general procedure was used. The polar phase propylene glycol was mixed with surfactant and co-surfactant in a heated container at about 60° C. to about 70° C. until the chemicals were completely melted. The non-polar oil phase was added to the mixture with moderate agitation for about 10 minutes, and then cooled to room temperature. At this point the lotion was in clear liquid form and ready to apply to the substrate. The micro-emulsion formed spontaneously without the need for a high shear mechanical device and is stable indefinitely.

Examples 2 to 8 were prepared in accordance with U.S. Pat. No. 7,169,400 to Luu et al., the disclosure of which is incorporated herein by reference. These lotion formulas were liquid at room temperature, transparent, very stable and accordingly the lotion ingredient ratios were inside the micro-emulsion region of phase diagrams such as FIG. 5 which is a partial phase diagram of the composition of Example 2. Surprisingly, the lotion of the present invention is characterized as having a good hand-feel perception and non-greasy hand-feel, which is thought to be due to the particle size of the micro-emulsion being too small to be detected in the oil phase by the fingertips.

TABLE 1

| Ingredients | Ex. 2 (%) | Ex. 3 (%) | Ex. 4 (%) | Ex. 5 (%) | Ex. 6 (%) | Ex. 7 (%) | Ex. 8 (%) |
|---|---|---|---|---|---|---|---|
| Propylene glycol | 35 | 35 | 5 | 15 | 15 | 30 | 35 |
| Finsolv TN[1] | 12.5 | 0 | 16 | 0 | 30 | 15 | 0 |
| Carnation oil[2] | 0 | 0 | 0 | 0 | 0 | 0 | 12.5 |
| Isopropyl myristate | 0 | 15 | 0 | 30 | 0 | 0 | 0 |
| Lambert CE 2000[3] | 0 | 0 | 4 | 0 | 0 | 0 | 0 |
| Myristyl alcohol($C_{14}$) | 12.5 | 15 | 0 | 0 | 0 | 0 | 12.5 |
| Kalcol 1618[4] | 0 | 0 | 7.5 | 0 | 5.5 | 5.5 | 0 |
| Glucam P-20 Distearate[5] | 0 | 0 | 67.5 | 0 | 49.5 | 49.5 | 0 |
| Glucamate SSE-20[6] | 40 | 35 | 0 | 55 | 0 | 0 | 40 |

[1] Finsolv TN: $C_{12}$-$C_{15}$ alkyl benzoate ester from Finetex Inc.
[2] Carnation: Mineral oil from Witco Corp.
[3] Lambert CT 2000 - tri-octyldodecyl-citrate (Guerbet ester) from Lambert Technologies.
[4] Kalcol 1618: Mixture 50/50 of cetyl alcohol (C16) and stearyl alcohol (C18) from Kao Corp.
[5] Glucan P-20 Distearate: PEG-20 methyl glucose distearate from Amer-chol.
[6] Glucamate SSE-20: PEG-20 methyl glucose sesquistearate from Amer-chol.

Example 9

The lotion prepared in Example 2 was applied to a tissue basesheet at a 5% add-on level, then converted to a two ply tissue product. The product was tested for the amount of lotion transferred to the skin. The results were compared with commercially available lotioned tissues by comparing the light reflection of cold lotion residual on glass relative to that from two other products. The scattering of light caused by lotion smeared onto the glass microscope slide was measured by using the UV/visible spectrophotometer in the wavelength region from 700 nm to 400 nm. Lotion was transferred to the slide by holding it between two layers of lotioned tissue for 30 seconds and then rubbing the tissue over the slide 20 times in 15 seconds. The lotion smeared glass slide was placed in the sample beam of a double beam UV/visible spectrometer to measure the light scattering. The results show that scattering of light caused by lotion smeared onto the slide rubbed with the tissue treated with the lotion in Example 1, looked identical to the control (untreated tissue). However, the two commercially available lotioned facial tissue products tested produced a significant amount of light scattering compared to the lotioned tissue of the present invention. In fact, the containers for these commercial products specifically state "not recommended for cleaning eyeglasses." In addition, from the lab test result, the amount of lotion transferred by the lotioned substrate of the present invention to the skin was measured to be about 4.2 mg/cm$^2$.

The lotioned substrate product of the present invention was able to transfer lotion to the skin for enhancing skin care benefits, while also being able to "wipe eyeglasses and still maintain clear vision." These properties of the present invention represent significant advantages over the lotioned facial tissues of the prior art.

The waterless emulsion compositions of the present invention have numerous attributes which make them particularly suitable for paper towels. For one, the waterless micro-emulsions form low viscosity aqueous micro-emulsions with relatively small amounts of water such that an immobilized lotion on the substrate is restorable to readily transferable form when wetted or mixed with water. Thus, when contacted with wet hands of a paper towel user, for example, the lotion is readily transferred from the towel to the skin of a user.

Another unique characteristic of the invention is that the lotion emulsions are capable of forming viscous gels with water as the amount of water mixed with the lotion is increased. Gels are generally more glutinous than liquids, thus being more desirable as hand lotions.

Details as to these characteristics appear in Examples 10-17 below.

Examples 10-17

The composition of Example 1 was mixed with water and tested for viscosity using a Brookfield Digital Viscometer at 73° F. Examples 10, 11, 12 and 17 were tested with a No. 2 spindle, while Examples, 13, 14, 15 and 16 were tested with a No. 5 spindle. Details as to composition and test conditions appear in Table 2 below.

TABLE 2

Aqueous Phasing Properties

| Example #/ Description | Spindle # | Speed (RPM) | Viscosity (cps) | Appearance and Properties |
|---|---|---|---|---|
| 10/100% Lotion Example #1 | 2 | 50 | 182 | Clear Liquid |
| 11/95% Lotion Example #1 + 5% Water | 2 | 50 | 218 | Clear Liquid |
| 12/90% Lotion Example #1 + 10% Water | 2 | 50 | 348 | Clear Liquid |
| 13/85% Lotion Example #1 + 15% Water | 5 | 10 | 4,600 | Viscous gel |
| 14/80% Lotion Example #1 + 20% Water | 5 | 10 | 22,000 (2) | Elastic gel |
| 15/70% Lotion Example #1 + 30% Water | 5 | 10 | 13,000 (2&3) | Crystalline gel |
| 16/50% Lotion Example #1 + 50% Water | 5 | 10 | 3,500 | Viscous turbid gel |
| 17/20% Lotion Example #1 + 80% Water | 2 | 50 | 140 | Turbid emulsion |

It is seen in Table 2 that the water/emulsion mixtures remained a micro-emulsion up to a water concentration of between 10% and 15% by weight of the composition (Examples 10-13). At 15% water, the lotion emulsion turned into a viscous gel, which became even more viscous as additional water was added. At 20% water, the composition was an elastic gel having a viscosity of 22,000 cps, making viscosity measurement difficult. At 30% water (Example 15), the gel exhibited some opacity and appeared to have some crystalline structure appearing almost brittle. Due to the difficulty of viscosity measurement as well as the elastic and adhesive properties of the elastic gel of Example 14, the actual difference in viscosity between Examples 14, 15 may be less than indicated in Table 2.

At 50% by weight water, viscosity fell off dramatically and the composition appeared to be a viscous, turbid gel which was somewhat translucent. While the viscosities of Examples 13 and 16 were similar, the composition of Example 15 exhibited considerably more turbidity. At 80% water, viscosity was low again; however, the composition was no longer clear and appeared to be an emulsion which was somewhat turbid.

Figure 6:
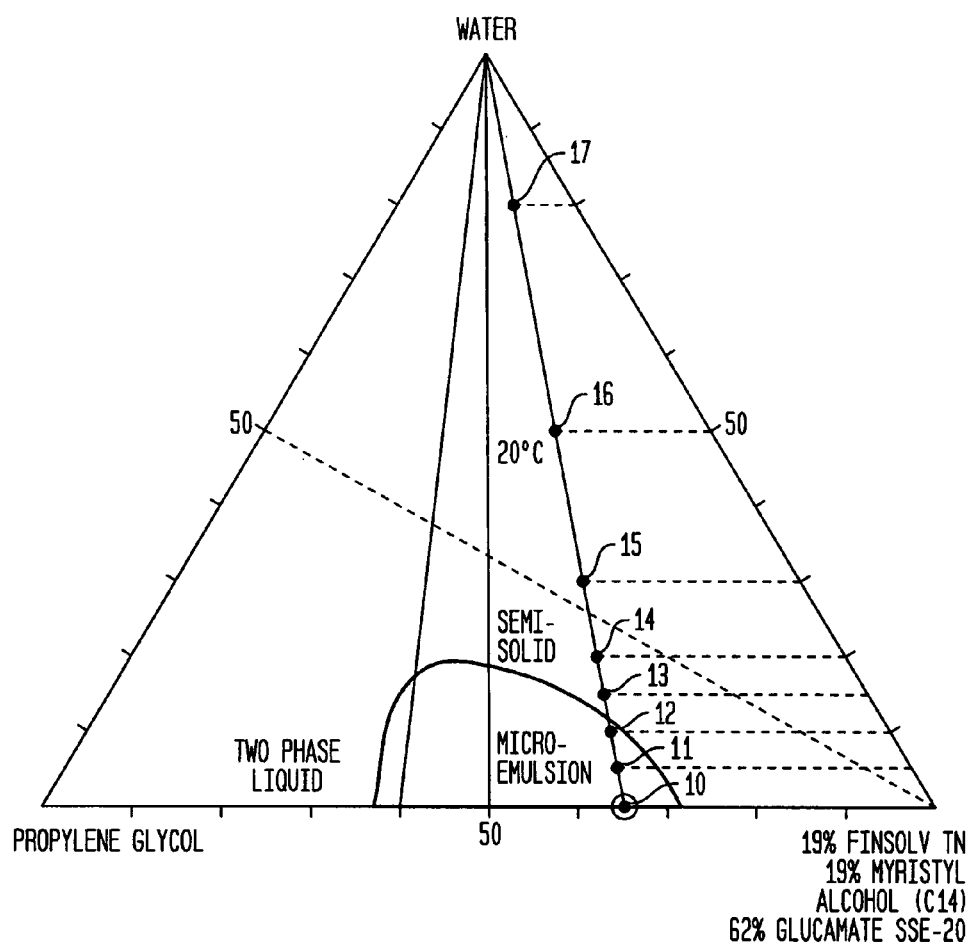
FIG. 6 is a partial phase diagram of the composition of Example 2 with water showing the phase behavior of a mixture of the composition of Example 2 with water.

The phase behaviors of the mixtures of Table 2 are illustrated in the partial phase diagram of FIG. 6, where it is seen that Examples 10, 11 and 12 are within the micro-emulsion region of the phase diagram. Examples 13, 14, 15 and 16 are in "semi solid" form, while Example 17 is a two-phase liquid.

Example 18 and Comparative Example A

Still further features of the invention which are highly desirable include WAR delay which promotes lotion transfer to the skin and anti-microbial action of paper towel. These features are appreciated from the discussion which follows.

Towel basesheet was prepared using 100% Douglas Fir Kraft fiber by way of a fabric crepe/Yankee dry process of the class disclosed in co-pending Provisional Application No. 60/693,699, entitled "Fabric-Creped Sheet for Dispensers", filed Jun. 24, 2005, the relevant disclosure of which is incorporated herein by reference in its entirety. To the basesheet, lotion was applied in 1" bands along the machine direction (alternating with 1" bands of unlotioned towel) using a Dynatec™ applicator of the class seen in U.S. Pat. Nos. 5,904,298; 5,902,540; and 5,882,573, the disclosures of which are incorporated herein by reference. The lotion formulation of Example 1 was used, containing additionally 2% by weight lotion triclosan anti-microbial compound, 2,4,4'-trichloro-2'-hydroxy diphenyl ether. Further details appear in Table 3 below.

The towel was treated for anti-microbial properties by placing a wetted specimen disk of towel in a Petri dish on inoculated agar. The anti-microbial properties are termed "negative" if microbe contamination is observed on or at the towel after incubation and "positive" if a "ring" around the test specimen is observed, indicating that microbe growth was inhibited by the towel.

Results of anti-microbial testing also appear in Table 3.

TABLE 3

Anti-microbial and Towel Properties

| Properties | Example A No Lotion | Example 18 Lotioned |
|---|---|---|
| Anti-microbial Properties: | | |
| *Staphylococcus aureus* | Negative | Positive |
| *E. coli* | Negative | Positive |
| *Salmonella* sps | Negative | Positive |
| Physical Properties: | | |
| Add on rate (% of product weight) | 0% | 8 to 10% |
| Basis Weight (lbs/rm) | 22.2 | 23.5 |
| Caliper (mils/8 sheets) | 46.0 | 46.1 |
| Dry MD Tensile (g/3") | 6531.2 | 5528.9 |
| Dry CD Tensile (g/3") | 3912.0 | 3435.1 |
| MD Stretch (%) | 7.4 | 7.7 |
| CD Stretch (%) | 3.3 | 3.7 |
| Wet MD Cured Tensile (g/3") (Finch) | 1976.1 | 2040.1 |
| Wet CD Cured Tensile (g/3") (Finch) | 1041.0 | 1122.1 |
| WAR (seconds) (TAPPI) | 34.3 | 67.6 |
| MacBeth 3100 Brightness (%) UV Excluded | 77.5 | 75.5 |
| Opacity (%) | 60.2 | 56.6 |
| SAT Capacity (g/m$^2$) | 125.1 | 123.0 |
| SAT Time (seconds) | 643.7 | 823.6 |
| GM Break Modulus | 1025.2 | 829.0 |

It is seen in Table 3 that the anti-microbial lotion was effective against *staphylococcus aureus, E. coli* and *salmonella* sps.

It is also seen that, with the absorbent capacity (SAT) of the control and the lotioned towel remained substantially the same, WAR times, or absorption rates were considerably lengthened, perhaps due to gel blockage; consistent with the data in Table 2 above. Higher WAR values are generally not desired; however, the glutinous gel feel and initial "wetness" experienced by a towel user is a positive consequence, offsetting lower measured absorption rates and encouraging more wiping action so the anti-microbial lotion is more effective in preventing or ameliorating contamination. The apparent gel blockage also appeared to increase CD wet tensile, a common source of towel failure.

Examples 19-23

The lotion compositions in the following examples comprise a base lotion with and without a pH balancing agent. Examples 19 and 20 are comparative and contain no pH balancing agent, and Examples 21-23 relate to lotion compositions combined with a pH balancing agent. Further detail is seen in U.S. Pat. No. 6,352,700, the disclosure of which is incorporated herein in its entirety.

The lotions in Examples 21-23 were prepared according to the following procedure: the base lotion ingredients, i.e., emollient(s), release and retention agent and surfactants were mixed together and heated to 75° C. until the mixture was completely melted. Note lotion composition components in Table 7. The lotion composition mixture was maintained at 75° C. for about 15 minutes with moderate agitation. The pH balancing compound was then added, using high agitation, until the compound was completely melted and blended. The pH value for each lotion was determined by emulsifying 0.276 g of solid lotion (equivalent to the lotion amount contained in 5 sheets of 15% lotionized tissue) in 20 ml tap water (pH=8.65) at 23° C. The emulsion was shaken for 5 minutes before measuring pH using a standard calibrated pH meter.

TABLE 4 pH Balanced Lotions

| Chemicals | Example 19 (%) | Example 20 (%) | Example 21 (%) | Example 22 (%) | Example 23 (%) |
|---|---|---|---|---|---|
| Finsoly TN-C12-C15 alkyl benzoate | 30 | 35 | 35 | 30 | 30 |
| Crodacol CS 50 (Cetearyl alcohol) | 57 | 65 | 63 | 56 | 55 |
| Clucate SS (methyl glucose sesquistearate) | 3 | 0 | 0 | 3 | 3 |
| Glucamate SSE-20 (PEG-20 methyl glucose sesquistearate) | 10 | 0 | 0 | 10 | 10 |
| Glycolic acid | 0 | 0 | 2 | 1 | 0 |
| Lactic acid | 0 | 0 | 0 | 0 | 2 |
| pH | 7.8 | 7.2 | 4.6 | 4.9 | 5.3 |

While the invention has been described in connection with numerous examples, modifications to those examples within the spirit and scope of the invention will be readily apparent to those of skill in the art. In view of the foregoing discussion, relevant knowledge in the art and references including co-pending applications discussed above, the relevant disclosures of which are all incorporated herein by reference, and further description is deemed unnecessary.

What is claimed is:

1. An antimicrobial paper towel with a chromatic transfer indicator comprising:
   a) a cellulosic web;
   b) a transferable lotion composition comprising an emollient and anti-microbial agent, the lotion composition being immobilized on the cellulosic web in a semi-solid or solid form and selected and applied in amounts such that it imparts a water absorption rate delay of at least about 25% to the cellulosic web,
   wherein the transferable lotion composition is selected from lotion compositions which are transferable upon contact with water or lotion compositions which are transferable upon application of heat;
   c) a water soluble pH balancing agent disposed on the web at a plurality of discrete pH balancing agent locations; and
   d) a pH-sensitive transfer indicator disposed on the web at a plurality of discrete indicator locations which are apart from the pH balancing agent locations, wherein the pH-sensitive transfer indicator is chromatically responsive to the pH balancing agent in aqueous form;
   wherein the pH balancing agent and the pH-sensitive transfer indicator are selected and applied to the web such that the pH-sensitive transfer indicator undergoes a gradual color change upon contact of the paper towel with water to indicate effective transfer of the lotion, wherein the initiation of said color change is determined by the wicking time of the pH balancing agent.

2. The anti-microbial paper towel according to claim 1, wherein the lotion composition comprises from about 0.01% to about 10% by weight anti-microbial agent.

3. The anti-microbial paper towel according to claim 1, wherein the lotion composition comprises from about 0.05% to about 5% by weight anti-microbial agent.

4. The anti-microbial paper towel according to claim 1, comprising an anti-microbial agent selected from: 2,4,4'-trichloro-2'-hydroxydiphenyl ether; 3,4,4'-trichlorocarbanilide; 3,4,4'-trifluoromethyl-4,4'-d-ichlorocarbanilide; 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol; 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; chlorhexidine gluconate; miconazole; terconazole; butylparaben; ethylparaben; methylparaben; methylchloroisothiazoline; methylisothiazoline; a mixture of 1,3-bis(hydroxymethyl)-5,5-dimethylhydantoin and 3-iodo-2-propynyl butyl carbamate; oxyquinoline; EDTA; tetrasodium EDTA; p-hydroxylbenzoic acid ester; alkyl pyridinum compounds; coco phosphatidyl PG-dimonium chloride; chlorhexidene digluconate; chlorhexidene acetate; chlorhexidene isethionate; chlorhexidene hydrochloride; benzalkonium chloride; benzethonium chloride; polyhexamethylene biguanide, and mixtures thereof.

5. The anti-microbial paper towel according to claim 1, wherein the anti-microbial agent is 2,4,4'-trichloro-2'-hydroxydiphenyl ether.

6. The anti-microbial paper towel according to claim 1, wherein the anti-microbial agent comprises a benzalkonium chloride.

7. The anti-microbial paper towel according to claim 1, wherein the anti-microbial agent comprises a zinc salt.

8. The anti-microbial paper towel according to claim 1, wherein the pH balancing agent comprises an organic acid.

9. The anti-microbial paper towel according to claim 1, wherein the pH balancing agent comprises an organic acid and a buffer combination.

10. The anti-microbial paper towel according to claim 9, wherein the buffer combination comprises citric acid and disodium phosphate.

11. The anti-microbial paper towel according to claim 9, wherein the buffer combination comprises disodium citrate and sodium hydroxide.

12. The anti-microbial paper towel according to claim 1, wherein the pH balancing agent is applied to the web in an amount of from about 0.5% to about 3% by weight of the lotion composition.

13. The anti-microbial paper towel according to claim 1, wherein the pH balancing agent is applied to the web in an amount of from about 1% to about 2% by weight of the lotion composition.

14. The anti-microbial paper towel according to claim 1, wherein the pH balancing agent comprises an alpha hydroxy acid, an alpha di-hydroxy acid, a beta hydroxy acid or combinations thereof.

15. The anti-microbial paper towel according to claim 14, wherein the pH balancing agent is selected from glycolic acid, alpha-acetyl glycolic acid, lactic acid, tartaric acid, alpha-acetyl lactic acid, alpha-hydroxy isobutyric acid, salicylic acid, mandelic acid, ortho-acetyl mandelic acid, benzilic acid, ortho-acetyl benzilic acid, malic acid, citric acid, gluconic acid, pyruvic acid, sorbic acid and combinations thereof.

16. The anti-microbial paper towel according to claim 14, wherein the pH balancing agent is citric acid.

17. The anti-microbial paper towel according to claim 14, wherein the pH balancing agent is lactic acid.

18. The anti-microbial paper towel according to claim 14, wherein the pH balancing agent is glycolic acid.

19. The anti-microbial paper towel according to claim 1, wherein the pH-sensitive transfer indicator comprises thymol blue, bromo cresol purple, methyl red, cresol red, phenolphthalein, thymolphthalein, or Alizarin yellow R.

20. The anti-microbial paper towel according to claim 1, wherein the pH-sensitive transfer indicator is thymol blue.

21. The anti-microbial paper towel according to claim 1, wherein the cellulosic web is predominantly softwood fiber.

22. The anti-microbial paper towel according to claim 1, wherein the web comprises a wet strength agent.

23. The anti-microbial paper towel according to claim 22, wherein the wet strength agent is selected from aldehyde-containing polyols, aldehyde-containing cationic starch, glyoxal, glutaraldehyde, dialdehydes, boric acid carbonate, zirconium ammonium carbonate, glyoxalated polyacrylamide, polyamide-epichlorohydrin, polyamine-epichlorohydrin, urea-formaldehyde, melamine-formaldehyde, polyethyleneimine, and latex emulsions.

24. The anti-microbial paper towel according to claim 1, wherein the transferable lotion composition disposed on the web is selected and applied in amounts such that it imparts a water absorption rate delay to the cellulosic web of at least about 50%.

25. The anti-microbial paper towel according to claim 1, wherein the transferable lotion composition disposed on the web is selected and applied in amounts such that it imparts a water absorption delay to the cellulosic web of at least about 75%.

26. The anti-microbial paper towel according to claim 1, wherein the transferable lotion composition disposed on the web is selected and applied in amounts such that it imparts a water absorption delay to the cellulosic web of at least about 100%.

27. The anti-microbial paper towel according to claim 1, wherein the unlotioned cellulosic web has substantially the same SAT value as the lotioned paper towel.

28. The anti-microbial paper towel according to claim 1, wherein the paper towel has a SAT value of at least about 2 g/g.

29. The anti-microbial paper towel according to claim 1, wherein the paper towel has a SAT value of at least about 3 g/g.

30. The anti-microbial paper towel according to claim 1, wherein the paper towel has a SAT value of at least about 4 g/g.

31. The anti-microbial paper towel according to claim 1, wherein the paper towel has a SAT value of at least about 4.5 g/g.

32. The anti-microbial paper towel according to claim 1, wherein the paper towel has a SAT value of from about 2 g/g to about 5 g/g.

33. The anti-microbial paper towel according to claim 1, wherein the paper towel has a WAR value of at least about 40 seconds.

34. The anti-microbial paper towel according to claim 1, wherein the paper towel has a WAR value of at least about 50 seconds.

35. The anti-microbial paper towel according to claim 1, wherein the paper towel has a WAR value of from about 55 seconds to about 75 seconds.

36. The anti-microbial paper towel according to claim 1, wherein the paper towel has a WAR value of at least about 100 seconds.

37. The anti-microbial paper towel according to claim 1, wherein the paper towel has a WAR value of at least about 120 seconds.

38. The anti-microbial paper towel according to claim 1, wherein the paper towel has a WAR value between bout 75 seconds and 200 seconds.

39. The anti-microbial paper towel according to claim 1, wherein the transferable lotion is applied to the cellulosic web in an amount of from about 3 weight percent to about 20 weight percent.

40. The anti-microbial paper towel according to claim 1, wherein the transferable lotion is applied to the cellulosic web in an amount of from about 5 percent by weight to about 15 percent by weight.

41. The anti-microbial paper towel according to claim 1, wherein the transferable lotion is applied to the cellulosic web in an amount of from about 8 percent by weight to about 10 percent by weight.

42. The anti-microbial paper towel according to claim 1, wherein the unlotioned cellulosic web has a basis weight of from about 15 $g/m^2$ to about 65 $g/m^2$.

43. The anti-microbial paper towel according to claim 1, wherein the unlotioned cellulosic web has a basis weight of from about 25 $g/m^2$ to about 50 $g/m^2$.

44. The anti-microbial paper towel according to claim 1, wherein the unlotioned cellulosic web has a basis weight of from about 30 $g/m^2$ to about 40 $g/m^2$.

45. The anti-microbial paper towel according to claim 1, wherein the cellulosic web comprises at least about 65 percent by weight softwood fiber.

46. The anti-microbial paper towel according to claim 1, wherein the cellulosic web comprises at least about 70 percent by weight softwood fiber.

47. The anti-microbial paper towel according to claim 1, wherein the cellulosic web comprises from about 70 percent by weight softwood fiber to about 90 percent by weight softwood fiber.

48. The anti-microbial paper towel according to claim 1, wherein the cellulosic web is predominantly comprised of fiber selected form softwood fiber, recycle fiber and mixtures thereof.

49. The anti-microbial paper towel according to claim 1, wherein the cellulosic web comprises at least 50 percent by weight recycle fiber.

50. The anti-microbial paper towel according to claim 1, wherein the cellulosic web comprises at least 60 percent by weight recycle fiber.

51. The anti-microbial paper towel according to claim 1, wherein the cellulosic web comprises at least 70 percent by weight recycle fiber.

52. The anti-microbial paper towel according to claim 1, wherein the cellulosic web comprises at least 80 percent by weight recycle fiber.

53. The anti-microbial paper towel according to claim 1, wherein the cellulosic web comprises at least 90 percent by weight recycle fiber.

54. The anti-microbial paper towel according to claim 1, wherein the fiber in the cellulosic web is 100% recycle fiber.

55. The anti-microbial paper towel according to claim 1, wherein the cellulosic web consists predominantly of Douglas fir fiber.

56. The anti-microbial paper towel according to claim 1, wherein the towel has an eight sheet caliper of from about 35 to about 90 mils, consists predominantly of softwood fiber and is in the form of a single ply towel.

57. The absorbent cellulosic sheet according to claim 1, wherein the cellulosic web comprises at least about 70 percent by weight Douglas fir fiber.

58. An anti-microbial paper towel comprising:
  a) a cellulosic web;
  b) a waterless micro-emulsion which is substantially liquid at room temperature immobilized on the web in a semi-solid or solid state and selected and applied in amounts such that it imparts a water absorption rate delay of at least about 75% to the cellulosic web;
  c) wherein, the waterless mien-emulsion comprises an anti-microbial agent, a polar emollient, a non-polar emollient and a surfactant composition including a non-ionic surfactant; and wherein further the waterless micro-emulsion is capable of forming an aqueous micro-emulsion upon contact with water;
  d) a water soluble balancing agent disposed on the web at a plurality of discrete pH balancing agent locations; and
  e) a pH-sensitive transfer indicator disposed on the web at a plurality of discrete indicator locations which are apart from the pH balancing agent locations, wherein the pH-sensitive transfer indicator is chromatically responsive to the balancing agent in aqueous form; and
wherein further the pH balancing agent and the pH-sensitive transfer indicator are selected and applied to the web such that the pH-sensitive transfer indicator undergoes a gradual color change upon contact with water to indicate effective transfer of the lotion, wherein the initiation of said color change is determined by the wicking time of the pH balancing agent.

59. A paper towel with a chromatic transfer indicator comprising:
  a) a cellulosic web;
  b) a water soluble pH balancing agent disposed on the web at a plurality of discrete pH balancing agent locations;
  c) a pH-sensitive transfer indicator disposed on the web at a plurality of discrete indicator locations which are apart from the pH balancing agent locations, wherein the pH-sensitive transfer indicator is chromatically responsive to the pH balancing agent in aqueous form; and
  d) a transferable lotion composition immobilized on the cellulosic web in a semi-solid or solid form and imparting a water absorption rate delay to the cellulosic web;
  wherein the pH balancing agent and the pH-sensitive transfer indicator are selected and applied to the web such that the pH-sensitive transfer indicator undergoes a gradual color change upon contact of the paper towel with water, wherein the initiation of said color change is determined by the wicking time of the pH balancing agent.

60. The paper towel according to claim 59, wherein the pH balancing agent is selected from glycolic acid, alpha-acetyl glycolic acid, lactic acid, tartaric acid, alpha-acetyl lactic acid, alpha-hydroxy isobutyric acid, salicylic acid, mandelic acid, ortho-acetyl mandelic acid, benzilic acid, ortho-acetyl benzilic acid, malic acid, citric acid, gluconic acid, pyruvic acid, sorbic acid and combinations thereof.

61. The paper towel according to claim 59, wherein the pH balancing agent is citric acid.

62. The paper towel according to claim 59, wherein the pH balancing agent is lactic acid.

63. The paper towel according to claim 59, wherein the pH balancing agent is glycolic acid.

64. The paper towel according to claim 59, wherein the pH-sensitive transfer indicator comprises thymol blue, bromo cresol purple, methyl red, cresol red, phenolphthalein, thymolphthalein, or Alizarin yellow R.

65. The paper towel according to claim 59, wherein the pH-sensitive transfer indicator is thymol blue.

* * * * *

UNITED STATES PATENT AND TRADEMARK OFFICE
CERTIFICATE OF CORRECTION

PATENT NO. : 8,388,992 B2  Page 1 of 1
APPLICATION NO. : 11/728407
DATED : March 5, 2013
INVENTOR(S) : Phuong Van Luu et al.

It is certified that error appears in the above-identified patent and that said Letters Patent is hereby corrected as shown below:

In the Specification

In column 23, line 46, delete "75%" and insert --25%--.
In column 23, line 47, delete "mien-emulsion" and insert --micro-emulsion--.

Signed and Sealed this
Fifth Day of November, 2013

Teresa Stanek Rea
*Deputy Director of the United States Patent and Trademark Office*